US012636434B2

(12) United States Patent
Zoglio

(10) Patent No.: US 12,636,434 B2
(45) Date of Patent: May 26, 2026

(54) FLOW RESTRICTION DEVICES, METHODS, AND SYSTEMS

(71) Applicant: NxStage Medical, Inc., Lawrence, MA (US)

(72) Inventor: Eric Zoglio, Derry, NH (US)

(73) Assignee: NxStage Medical, Inc., Lawrence, MA (US)

( * ) Notice: Subject to any disclaimer, the term of this patent is extended or adjusted under 35 U.S.C. 154(b) by 0 days.

(21) Appl. No.: 18/676,776

(22) Filed: May 29, 2024

(65) Prior Publication Data

US 2024/0307616 A1     Sep. 19, 2024

Related U.S. Application Data

(63) Continuation of application No. 17/441,919, filed as application No. PCT/US2020/023924 on Mar. 20, 2020, now Pat. No. 12,017,042.

(60) Provisional application No. 62/937,907, filed on Nov. 20, 2019, provisional application No. 62/822,117, filed on Mar. 22, 2019.

(51) Int. Cl.
    F16K 7/06         (2006.01)
    A61M 5/168         (2006.01)
(52) U.S. Cl.
    CPC .... A61M 5/16813 (2013.01); A61M 5/16877 (2013.01); F16K 7/06 (2013.01)
(58) Field of Classification Search
    CPC .. F16K 7/04; F16K 7/06; F16K 7/063; A61M 5/16877; A61M 5/16813; A61M 39/284; F04B 43/0081

USPC .............................................................. 251/9
See application file for complete search history.

(56) References Cited

U.S. PATENT DOCUMENTS

| | | | | | |
|---|---|---|---|---|---|
| 2,010,229 | A | * | 8/1935 | Goff | F16K 7/063 |
| | | | | | 251/9 |
| 2,183,835 | A | * | 12/1939 | Foulke | F16K 7/06 |
| | | | | | 251/5 |
| 2,527,614 | A | | 10/1950 | Arpin | |

(Continued)

FOREIGN PATENT DOCUMENTS

| | | | | | | |
|---|---|---|---|---|---|---|
| CN | 104415422 | A | * | 3/2015 | ........ | A61M 5/16804 |
| CN | 104415424 | A | * | 3/2015 | ........ | A61M 5/16881 |

(Continued)

OTHER PUBLICATIONS

Translation of CN 104415422 A (Year: 2015).*

(Continued)

*Primary Examiner* — Umashankar Venkatesan
(74) *Attorney, Agent, or Firm* — Potomac Law Group, PLLC

(57)                ABSTRACT

A flow restrictor includes a flexible tube held in a housing and a linear actuator connected through an intermediate link to a distal link via a first revolute joint proximate the linear actuator and a second revolute joint connecting the intermediate and distal links. The distal link has a distal end adjacent the flexible tube and the intermediate and distal links are constrained to move such that when the linear actuator moves the first revolute joint toward the linear actuator, the distal end of the distal link is driven into the side of the tube thereby progressively occluding the flexible tube.

6 Claims, 6 Drawing Sheets

(56)                References Cited

U.S. PATENT DOCUMENTS

| | | | |
|---|---|---|---|
| 3,156,444 A * | 11/1964 | Black | F16K 7/063 |
| | | | 251/285 |
| 3,308,898 A * | 3/1967 | Allen | B65B 39/001 |
| | | | 222/638 |
| 3,335,753 A | 8/1967 | Kiser | |
| 3,515,367 A * | 6/1970 | Theodore, Jr. | F16K 7/061 |
| | | | 251/9 |
| 3,759,483 A | 9/1973 | Baxter | |
| 3,861,421 A * | 1/1975 | Thompson | F16K 11/027 |
| | | | 251/9 |
| 3,930,761 A | 1/1976 | Barraclough | |
| 4,077,601 A * | 3/1978 | Dick | F16K 7/066 |
| | | | 81/331 |
| 4,178,975 A | 12/1979 | Crespi | |
| 4,323,219 A * | 4/1982 | Carlin | F16K 7/063 |
| | | | 251/5 |
| 4,372,345 A | 2/1983 | Mehus | |
| 4,544,127 A | 10/1985 | Szabo | |
| 5,191,881 A | 3/1993 | Beck | |
| 5,273,252 A * | 12/1993 | Brugalieres | F16L 55/10 |
| | | | 251/9 |
| 5,588,634 A | 12/1996 | Nettekoven | |
| 5,896,887 A | 4/1999 | Edwards | |
| 6,892,900 B2 * | 5/2005 | Drechsel | G05D 16/2086 |
| | | | 251/282 |
| 8,387,655 B2 | 3/2013 | Cowlishaw | |
| 2006/0129110 A1 | 6/2006 | Smith et al. | |
| 2009/0270844 A1 | 10/2009 | Seeley et al. | |

FOREIGN PATENT DOCUMENTS

| | | |
|---|---|---|
| CN | 109357038 A | 2/2019 |
| JP | S5662995 U | 5/1981 |
| WO | 2012014267 A1 | 2/2012 |

OTHER PUBLICATIONS

CN 104415424 A (Year: 2015).*
Extended European Search Report dated Nov. 8, 2022 for European Patent Application No. 20778728.4.
International Search Report and Written Opinion mailed Jul. 31, 2020 for International Patent Application No. PCT/US2020/023924.
Invitation to Pay Additional Fees dated May 21, 2020 for International Patent Application No. PCT/US2020/023924.
Written Opinion of the International Preliminary Examining Authority dated Mar. 12, 2021 for International Patent Application No. PCT/US2020/023924.

* cited by examiner

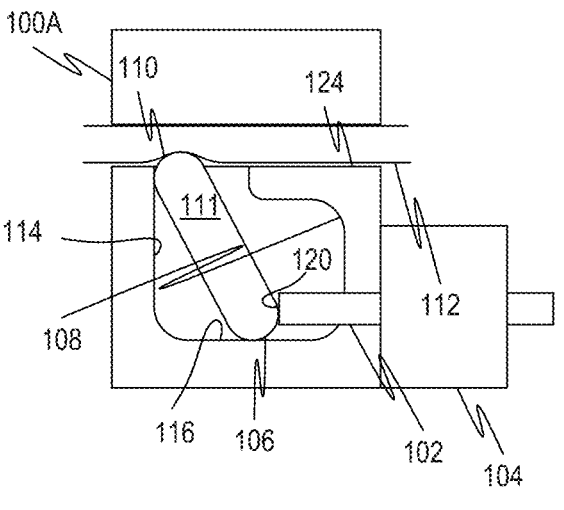
Fig. 1A
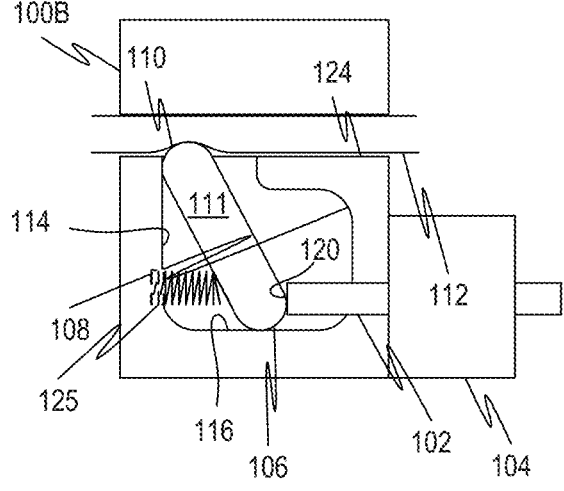
Fig. 1D
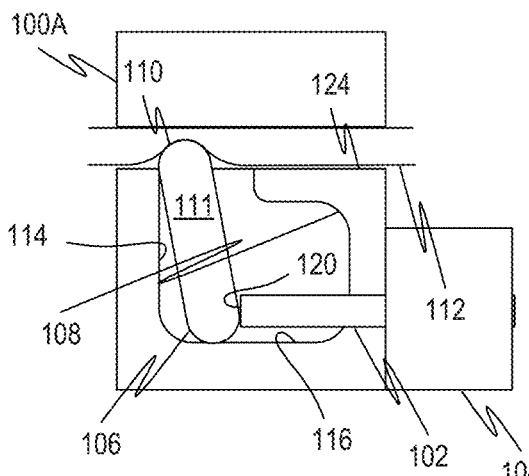
Fig. 1B
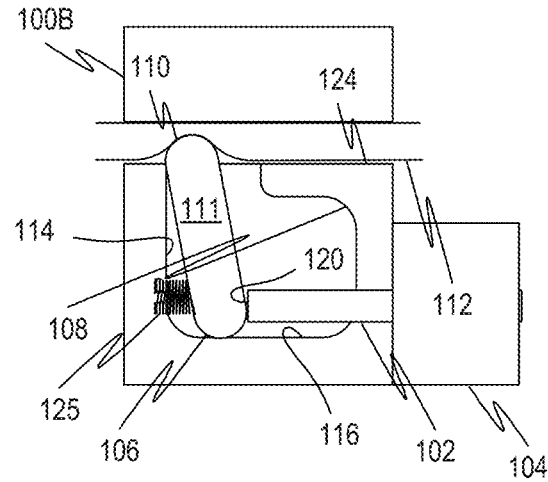
Fig. 1E
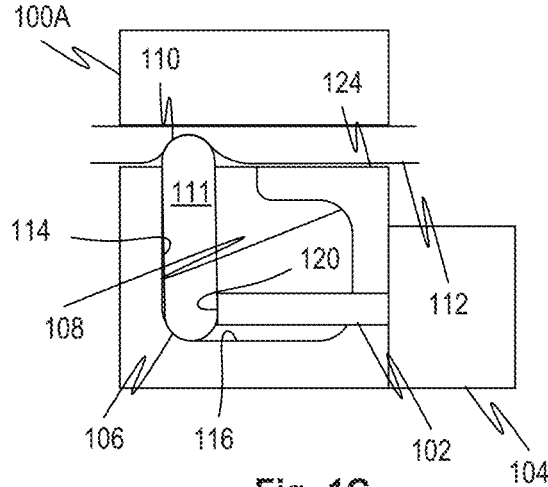
Fig. 1C
Fig. 1F

Mixing system

FLOW RESTRICTION DEVICES, METHODS, AND SYSTEMS

CROSS-REFERENCE TO RELATED APPLICATIONS

This Application is a continuation of U.S. application Ser. No. 17/441,919 filed Sep. 22, 2021, which is a U.S. national stage filing under 35 U.S.C. § 371 of International Application No. PCT/US2020/023924 filed Mar. 20, 2020, which claims priority to and the benefit of U.S. Provisional Patent Application No. 62/822,117 filed Mar. 22, 2019 and U.S. Provisional Patent Application No. 62/937,907 filed Nov. 20, 2019, all of which are hereby incorporated by reference in their entireties.

BACKGROUND

Various fluid management systems rely on the control of fluid flow rates. Commonly such systems employ variable rate pumps to regulate flow. Such systems tend to be expensive. For example, a system that regulates, or meters, flow for three fluids might require three separate pumps. If the pumps are peristaltic pumps then three separate pumping tube portions would be required for a disposable fluid circuit as well as the three separate actuators and their associated weight and cost.

SUMMARY

A variable pinch valve provides precise flow control by progressively pinching a tube. The pinching element creates a gradually-increasing mechanical advantage that increases the force pinching the tube as the tube approaches full occlusion. In embodiments, a system serves as a basis for a flow regulation system in which the variable pinch valves each controls the flow of a separate fluid. The fluids may be combined to form a mixture. Each fluid may be driven by a hydraulic source fluid which feeds a flexible-walled isolation element so the hydraulic source fluid does not mix with the separate fluids. The ratio of volumes of the separate fluids may be determined by the variable pinch valves and a relative flow therethrough.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIGS. 1A through 1C show a single action pinch valve without a spring according to embodiments of the disclosed subject matter.

FIGS. 1D through 1F show a single action pinch valve with a spring according to embodiments of the disclosed subject matter.

DETAILED DESCRIPTION

Figure 2A:
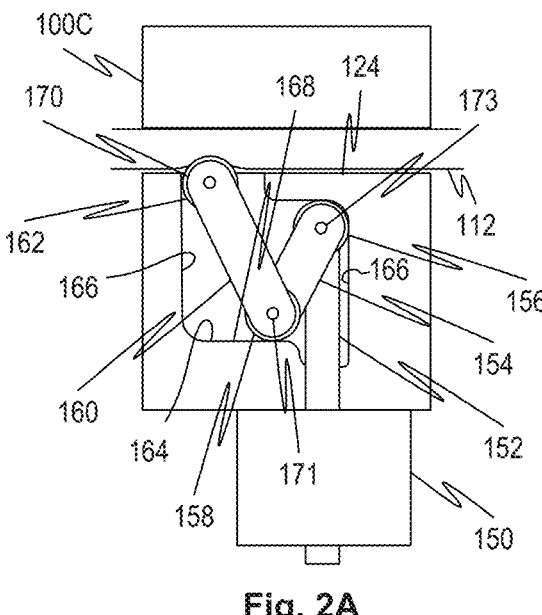
FIGS. 2A and 2B show a double action pinch valve without a spring according to embodiments of the disclosed subject matter.

Referring to FIGS. 1A through 1C, a tube support 100A has a hollow 108 that confines a free lever element 111. A tube 112 is held by a tube support 124. Free lever element 111 progressively pinches the tube 112 by pushing a pinching end 110 of the free lever element 111 into the tube 112 as an opposite driven end 106 of the free lever element 111 is pushed, by an end effecter 120 of a linear actuator 104, along a wall 116 causing the pinching end 110 to slide along a wall 114. More specifically, the linear actuator 104 has a rod 102 which can move in a linear direction (horizontal direction in FIGS. 1A-1F), and the rod 102 has at its end the end effecter 120, which is positioned to press on free lever element 111. In other words, the linear actuator 104 pushes the free lever element 111 so that it pivots and such that its pinching end 110 is driven into the side of the tube 112 thereby pinching it progressively closed. This motion creates a gradually-increasing mechanical advantage that increases the force pinching the tube 112 as the tube 112 approaches full occlusion. The displacement of the linear actuator 104 thereby determines the amount by which the tube 112 is pinched and thereby determines the cross-sectional area of the inside of the tube 112. This gradually changes the magnitude of a flow restriction represented by the tube 112.

Note that the engagement of the free lever with the walls 114 and 114 may be identified as joints, namely, sliding joints. Their engagement may also be identified as revolute joints. Thus an equivalent kinematic mechanism may be provided where the free lever is a link, through revolute joints, two sliding joints at the end of the free lever.

In FIG. 1A, the free lever element 111 is shown pinching the tube 112 to a small degree. In FIG. 1B, the free lever element 111 is shown pinching the tube 112 to a larger degree. In FIG. 1C, the free lever element 111 is shown pinching the tube 112 to a maximal degree, effectively fully occluding the tube 112 to prevent any flow therethrough.

When the linear actuator is withdrawn to pull away from the opposite driven end 106, the position of the free lever element 111 may be pushed back to a more relaxed position by the resilience of the tube 112 or the pressure of fluid within it. Alternatively, in a further embodiment 100B shown in FIGS. 1D through 1F, a spring 125 may be provided to return the free lever element 111 to a non-occluding or lower-occluding position. That is, the linear actuator 104 pushes the end effecter 120 into the opposite driven end 106, a side of the free lever element 111 is pushed against and compresses the spring 125. The spring may be partially recessed in the wall 114 as illustrated. A secondary function of the spring 125 is to prevent backlash. Note other types of springs may be provided such as leaf springs and this applies to any of the embodiments described or claimed. Note also that the spring 125 may be a tension spring with the function of preventing backlash in the linear actuator 104.

In FIG. 1D, the free lever element 111 is shown pinching the tube 112 to a small degree. In FIG. 1D, the free lever element 111 is shown pinching the tube 112 to a larger degree. In FIG. 1F, the free lever element 111 is shown pinching the tube 112 to a maximal degree, effectively fully occluding the tube 112 to prevent any flow therethrough. When the linear actuator withdraws by moving in progression shown by the sequence of FIGS. 1F, 1E, to 1D, the spring 125 pushes the free lever element opposite driven end 106 back along with the end effecter 120 following it backwards and withdrawing the pinching end of the free lever element away from the tube 112 thereby allowing the tube to relax. As a result the internal area of the tube 112 expands allowing progressively more flow.

Figure 2C:
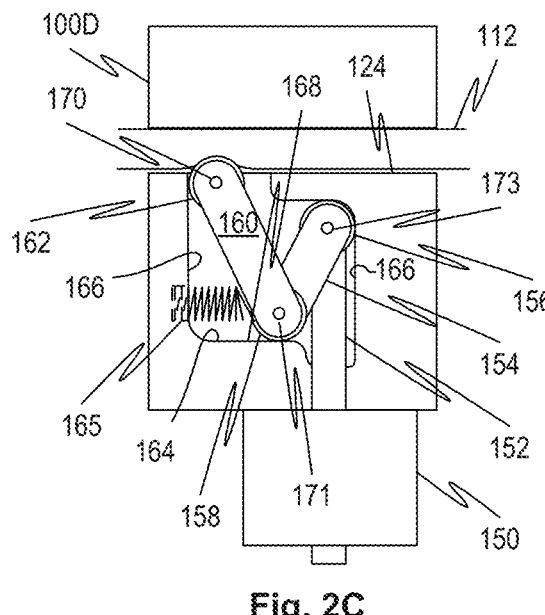
FIGS. 2C and 2D show a double action pinch valve with a spring according to embodiments of the disclosed subject matter.
Figure 2B:
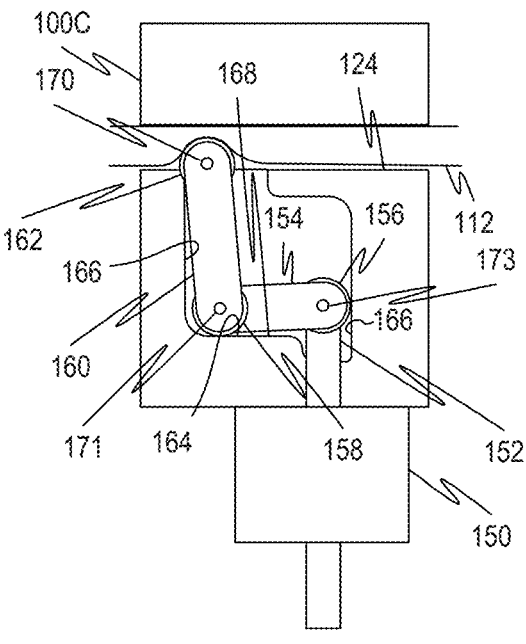
Figure 2B:
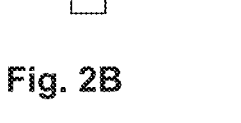

Referring to FIGS. 2A and 2B, another tube support 100C has a dual-action pinching mechanism. The pinching end 170 of a distal element 160 carries a roller 162. The distal element 160 is a link (and will also be referred to as link 160) connected to an intermediate link 154 by a revolute joint 171. The intermediate link 154 is connected to the effecter 152 of a linear actuator 150 by a revolute joint 173. Rollers 158 and 156 allow the revolute joints 171 and 173 to roll along the walls 164 and 166 of hollow 168, respectively. The tube 112 is held by tube support 124. The dual action motion of the link 154 generates a progressively-increasing mechanical advantage that increases the force pinching the tube 112 as the tube 112 approaches full occlusion. The linear actuator 150 extend withdraws the effecter 152 pulling the intermediate link 154 downwardly and forcing the roller 158 and the revolute joint 171 along the wall 164 thereby driving the roller 162 into the tube 112. The tube 112 is shown fully occluded in FIG. 2B and partially occluded in FIG. 2A.

Figure 2D:
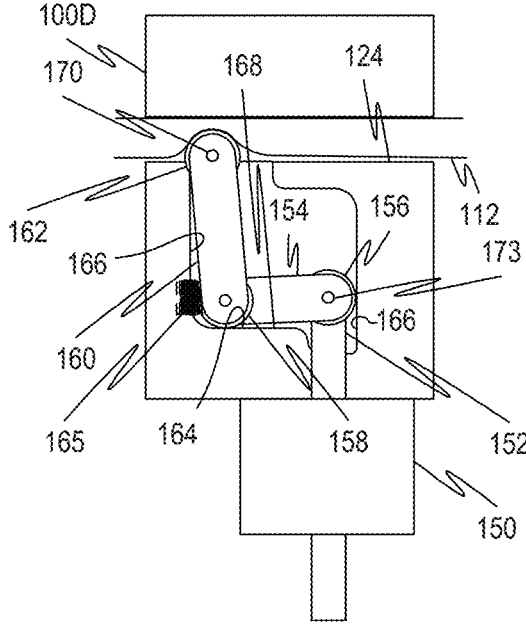

The linear actuator 150 may restore the links 154 and 160 to their non-occluding position due to the connection by the revolute joint 173 at the end of the effecter 152. That is, as the linear actuator 150 extends the effecter 152, the revolute joint 173 is pushed away from the linear actuator 150 causing the roller 156 to roll along the wall 166 and thereby causing the roller 158 to roll along wall 164 taking the revolute joint 171 with it. In other embodiments 100D, a spring 165 may be provided to reduce the force required to return the links 154 and 160. Such an embodiment is shown in FIGS. 2C and 2D. The spring 165 pushes the joint 171 away from the wall 166 to assist in causing the roller 162 to retract from the tube 112. Note that spring 165 may be a tension or compression spring. The function of the spring is to prevent backlash in the linear actuator 150.

Figure 3:
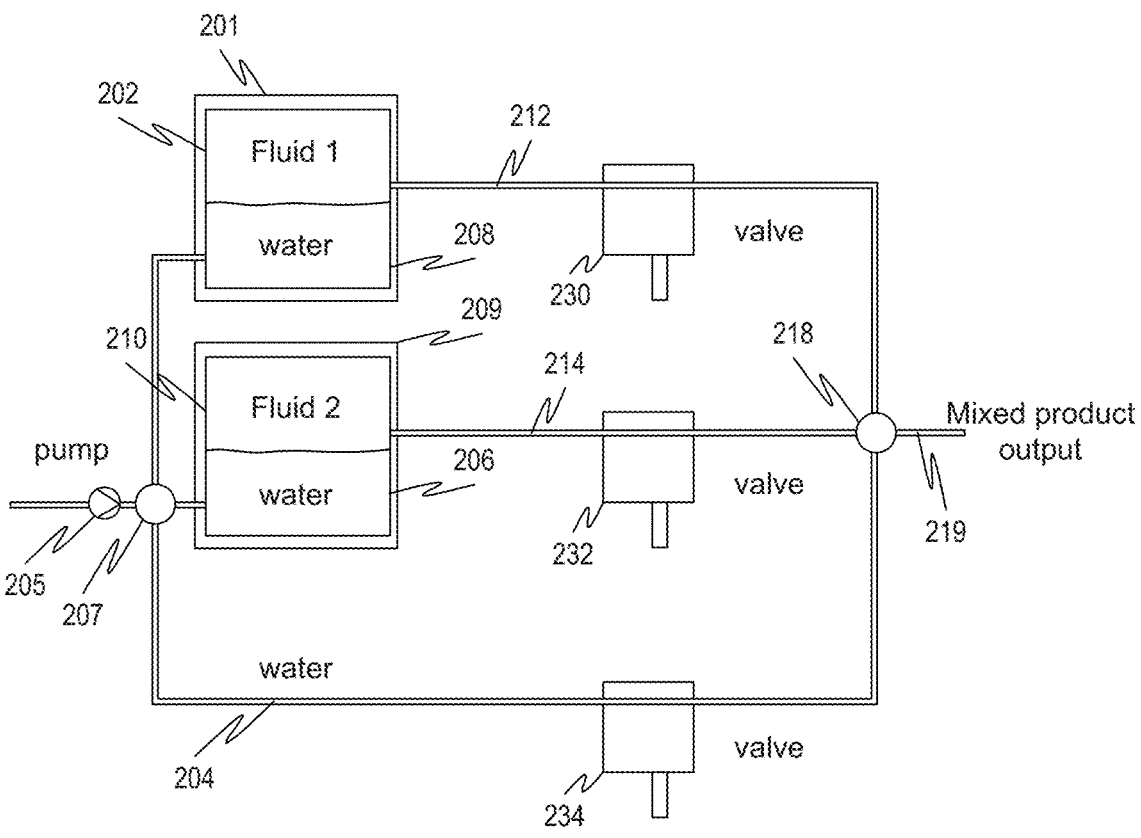
FIG. 3 shows a mixing system that mixes three separate fluids using a single pump and valves according to embodiments of the disclosed subject matter.

Referring to FIG. 3, a system embodiment employs multiple variable flow restrictors 230 to 234 to regulate, independently, flows of first fluid 202, second fluid 210 and water from second bag 206. A first fluid 202 is held in a bag in a confining container 201 with a second bag containing water 208 such that when water is pumped into the second bag 208, the first fluid 202 is forced out through a line 212 regulated by a variable flow restrictor 230. A second fluid 210 is held in a bag in a confining container 209 with a second bag containing water 206 such that when water is pumped into the second bag 206, the second fluid 210 is forced out through a line 214 regulated by a variable flow restrictor 232. The pressure of fluid in both bags 208 and 206 is maintained by a pump 205. A flow splitter 207 conveys fluid to the bags 208 and 206 and a line 204. Water flow is regulated through line 204 by a variable flow restrictor 234. The water from line 204 and the fluid in lines 212 and 214 may be mixed in a mixing unit 218 to produce a mixture at 219. The variable flow restrictors may be as described according to any of foregoing embodiments including 100A through 100D.

Figures 4A, 4B:
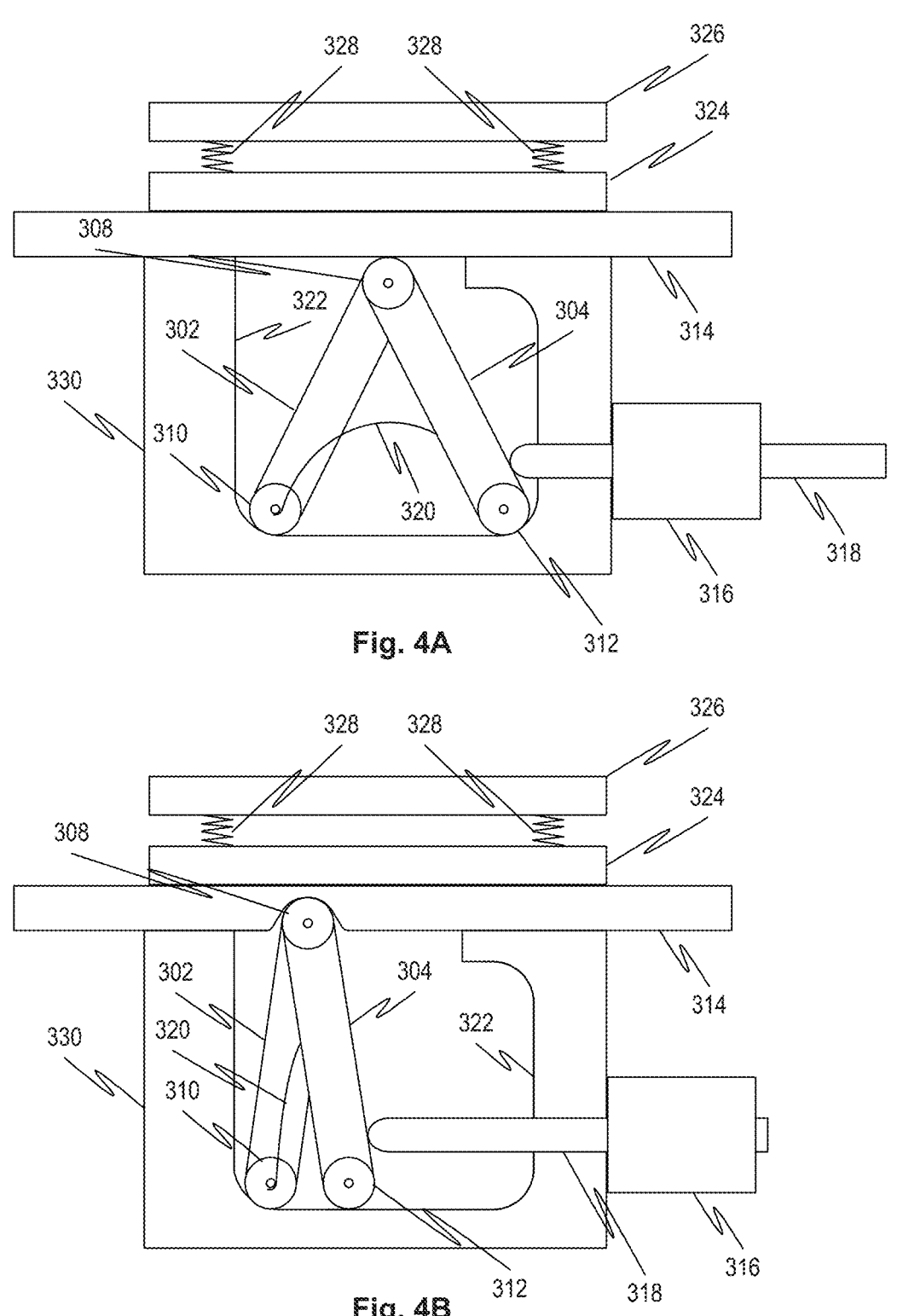
FIGS. 4A and 4B show another embodiment of a flow regulating pinch clamp, according to embodiments of the disclosed subject matter.

Referring now to FIGS. 4A and 4B, a further pinching mechanism configuration is shown. A pair of legs 302 and 304 are joined at a hinge with a roller 308 such that when one leg 304 is pushed toward the other, the roller 308 is pushed into the tube squeezing it closed. It will be observed that the force of the roller 308 rises with displacement of the leg 304 toward a maximum value in the position shown in FIG. 4B. A linear actuator 316 having an end effecter 318 pushes the leg 304 toward the leg 302. Roller 308 rolls along the tube 314 thereby squeezing the tube 314 closed as shown in FIG. 4B. A two-part tube support with pressure relief blocks 324 and 326 and spring 328 may be used to limit the amount of force that is applied to the tube 314. Rollers 310 and 312 roll along the recess 322. A leaf spring 320 prevents any backlash of the linear actuator 316 and the end effecter 318 by continuously applying a restoring force to the leg 304. The recess 322 is defined within a frame 330.

Figures 5A, 5B:
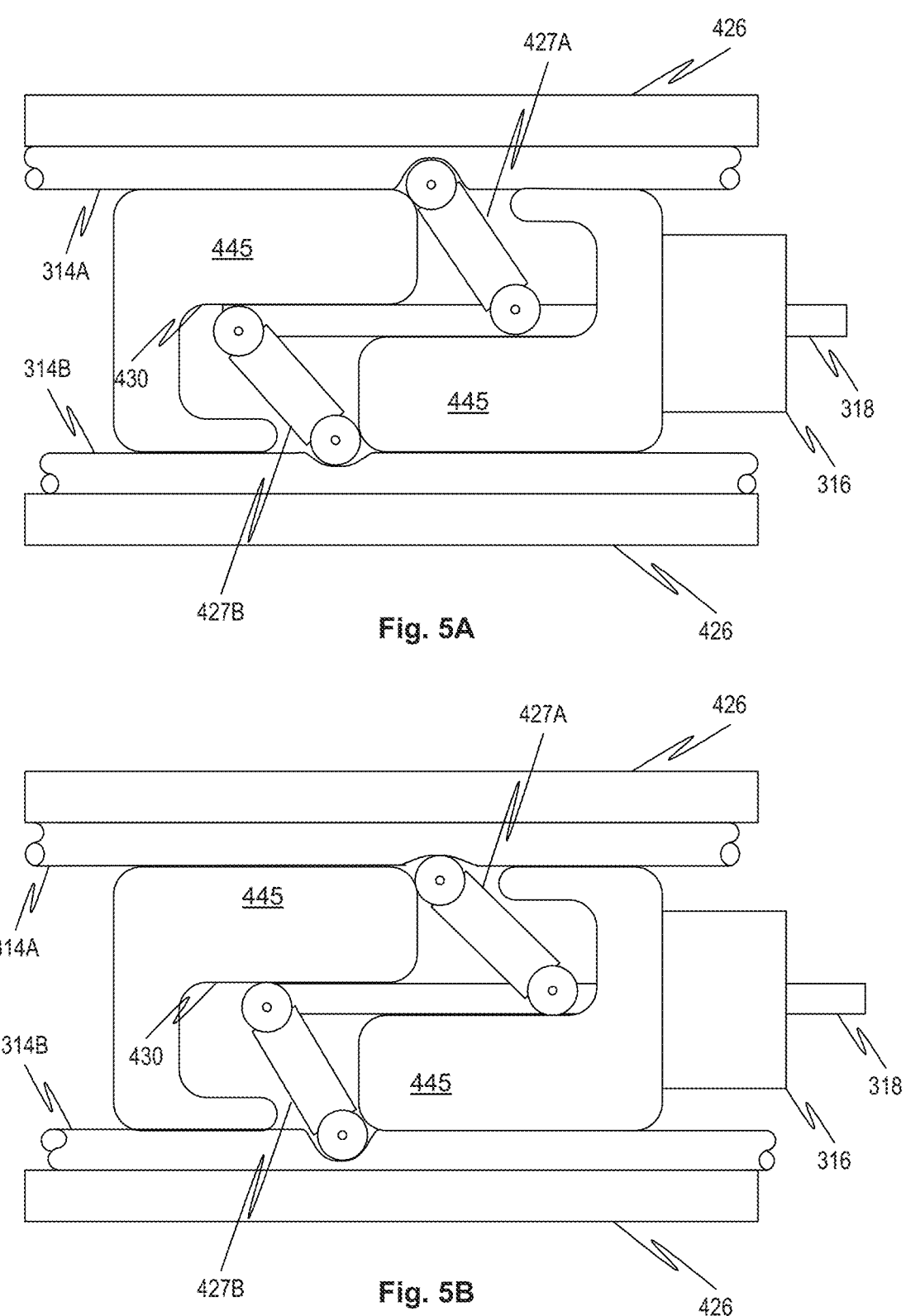
FIGS. 5A and 5B show an embodiment of a ratiometric proportioning system, according to embodiments of the disclosed subject matter.

Referring now to FIGS. 5A and 5B, a lever element 427A is driven by an end effecter 318 moved by a linear actuator 316. The lever element 427B is similarly driven by the end effector at its end. By moving the end effecter to the left, the lever element 427B releases pressure on a tube 314B while lever element 417B increase pressure on the tube 314A. In this way, the tubes are oppositely squeezed for a given motion of the end effecter. Note each tube is forced against a respective stop 426. Each lever element rides an internal surface 430 of a respective block element 445. In FIG. 5A, the tube 314B is shown being released by the lever element 427B and in FIG. 5B the same tube 314B is shown being squeezed. In FIG. 5A, the tube 314B is shown squeezed by the lever element 427B and in FIG. 5B the same tube 314B is shown being released. In this way the tubes can be ratiometrically pinched by the lever elements which are driven by a single linear actuator.

Figures 6A, 6B:
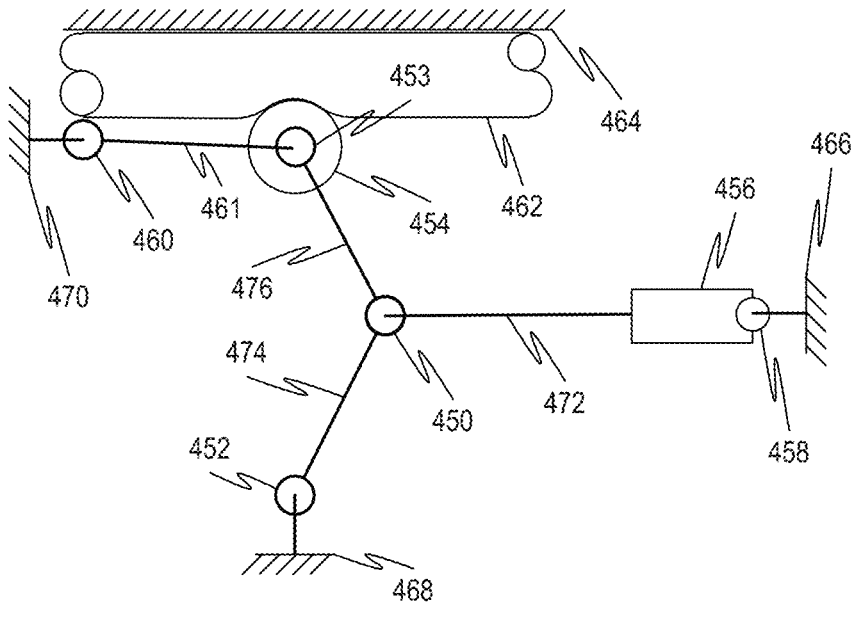
FIGS. 6A and 6B show an embodiment that does not rely on a linear motion constraint except for a linear actuator, according to embodiments of the disclosed subject matter.

Referring now to FIGS. 6A and 6B, a flow restrictor 459 has constraints, except for the linear actuator, that are all provided by links with revolute joints. In the present embodiment, referring specifically to FIG. 6A in which a tube 462 is only slightly pinched by a pinching effecter 454. The pinching effecter 454 is guided or constrained by a link 461 connected to a chassis portion 470 by a revolute joint 460. Chassis portion 470 may be fixedly connected to all the chassis portions 468, 466, and 464 to fixedly support all revolute joints 460, 452, and 458 as well as tube 462. That is, all the chassis portions may be parts of the same component such that none of them moves with respect to the others when the flow restrictor 459 is actuated to pinch the tube 462. The linear actuator 456 is supported on a revolute joint 458. The effecter 472 pushes on a pair of concentric revolute joints centered at 450 to drive links 474 and 476 to make the angle between them more or less obtuse depending on the direction of movement of the linear actuator 456. Note that pinching effecter 454 may revolve around revolute joint 453 or not. That is, the pinching effecter 454 may be fixedly attached to link 461 or 476 or it can revolve around the revolute joint 453 instead. Comparing FIG. 6A with FIG. 6B illustrates the operation of the mechanism shown and makes clear that only revolute joints, apart from the linear actuator, are required to push the pinching effecter 454 into the tube in the manner whereby the mechanical advantage increases as the tube is increasingly pinched.

An aspect common to embodiments disclosed herein includes the non-linearity of the relationship between pinching force delivered to the tube and the displacement of the linear actuator. In the case of the embodiments described, the pinching force the valve is capable of delivering for a given size motor increases as the linear actuator is displaced. This provides a benefit in that it takes more force to close a tube close to full occlusion than it takes to close it initially. Thus, it is possible to provide an automatic valve in which the power capability of the motor can be smaller than for a valve actuator that does not have this feature.

Another aspect common to embodiments disclosed herein is that the non-linear relationship between displacement of the motor and deformation of the walls of the tube by the part of the valve in contact with the tube which actually deforms it to reduce the flow. This is beneficial because for a given pressure, the relationship between the rate of flow and the deformation of the tube is also non-linear. That is, the flow rate drops less and less for each increment of displacement of the walls of the tube as the tube is pinched such that at the beginning of a closure, very little reduction in flow occurs and at the end of the closure a larger reduction in flow occurs. By coupling the non-linearity in relationship of displacement of the motor to the deformation of the walls with the non-linear relationship between deformation of the tube to incremental rate of change in flow, the relationship between the motor displacement and the change in flow rate becomes more linear.

Note that in any of the embodiments where linkages transfer force of the linear motor to a final element that pinches a tube, the linkages, collectively, will be understood to be a force transfer mechanism, a kinematic chain, a transmission, or other similar identifier of its function. Any sliding constraint may be identified as a joint, namely a sliding joint.

According to embodiments, the disclosed subject matter includes a variable flow restrictor with a tube support having a hollow with a flexible tube therein. A free lever element is trapped in the hollow. An actuator is configured to push the free lever element progressively such that it progressively pinches the tube against a first wall of said hollow.

In variations thereof, the foregoing embodiments includes ones in which the free lever element is a longitudinal member. In variations thereof, the foregoing embodiments includes ones in which the actuator is configured to push the free lever element such that an end thereof rides along second wall of said hollow. In variations thereof, the foregoing embodiments includes ones in which the free lever element is a longitudinal member and the actuator is configured to push one end thereof such that another end thereof rides along a second wall of said hollow. In variations thereof, the foregoing embodiments includes ones in which the hollow has second and third walls and the free lever element is a longitudinal member and the actuator is configured to push one end thereof such that said one end rides along the third wall while another end thereof rides along the second wall.

In variations thereof, the foregoing embodiments includes ones in which the actuator has first and second links connected by a revolute joint, a distal one of which is connected by a further revolute joint to the lever element. In variations thereof, the foregoing embodiments includes ones in which wheels are attached at each of the revolute joints. In variations thereof, the foregoing embodiments includes ones in which the first, second, and third walls are straight. In variations thereof, the foregoing embodiments includes ones in which the first link is connected to a linear actuator.

In variations thereof, the foregoing embodiments includes ones in which the free lever element is forced by a return spring.

According to embodiments, the disclosed subject matter includes a variable flow restrictor with a tube support having a hollow with a flexible tube therein. A free lever element is trapped in the hollow. An actuator is configured to push the free lever element progressively such that it progressively pinches the tube against a first wall of said hollow.

In variations of the foregoing embodiments, the free lever element is a longitudinal member. In variations of the foregoing embodiments, the actuator is configured to push the free lever element such that an end thereof rides along second wall of said hollow. In variations of the foregoing embodiments, the free lever element is a longitudinal member and the actuator is configured to push one end thereof such that another end thereof rides along a second wall of said hollow. In variations of the foregoing embodiments, the hollow has second and third walls and the free lever element is a longitudinal member and the actuator is configured to push one end thereof such that said one end rides along the third wall while another end thereof rides along the second wall. In variations of the foregoing embodiments, the actuator has first and second links connected by a revolute joint, a distal one of which is connected by a further revolute joint to the lever element. In variations of the foregoing embodiments, wheels are attached at each of the revolute joints. In variations of the foregoing embodiments, the first, second, and third walls are straight. In variations of the foregoing embodiments, the first link is connected to a linear actuator. In variations of the foregoing embodiments, the free lever element is forced by a return spring.

According to further embodiments, the disclosed subject matter includes a flow mixing system with a pump configured to generate a pressure applied to a first double chamber container such that a first fluid pumped by the pump is forced into a first side of the first double chamber transferring pressure through a flexible wall dividing the first double chamber to a second fluid in a second side of the double chamber. A first variable flow restrictor occludes a first flexible tube connected to the first double chamber second side. The pump is further configured to generate a pressure applied to a second double chamber container such that the first fluid pumped by the pump is forced into a first side of the second double chamber transferring pressure through a flexible wall dividing the second double chamber to a third fluid in a second side of the second double chamber. A second variable flow restrictor occludes the second flexible tube connected to the second double chamber second side. The first and second flexible tubes are connected to a flow mixer to generate a mixture of the second and third fluids responsively to the relative occlusion of the first and second variable flow restrictors.

In variations thereof, the further embodiments include embodiments in which the variable flow restrictor includes a tube support having a hollow with a flexible tube therein, a free lever element trapped in the hollow, an actuator configured to push the free lever element progressively such that it progressively pinches the tube against a first wall of said hollow.

In variations thereof, the further embodiments include embodiments in which the free lever element is a longitudinal member.

In variations thereof, the further embodiments include embodiments in which the actuator is configured to push the free lever element such that an end thereof rides along second wall of said hollow.

In variations thereof, the further embodiments include embodiments in which the free lever element is a longitudinal member and the actuator is configured to push one end thereof such that another end thereof rides along a second wall of said hollow.

In variations thereof, the further embodiments include embodiments in which the hollow has second and third walls and the free lever element is a longitudinal member and the actuator is configured to push one end thereof such that said one end rides along the third wall while another end thereof rides along the second wall.

In variations thereof, the further embodiments include embodiments in which the actuator has first and second links connected by a revolute joint, a distal one of which is connected by a further revolute joint to the lever element.

In variations thereof, the further embodiments include embodiments in which rollers are attached at each of the revolute joints.

In variations thereof, the further embodiments include embodiments in which the first, second, and third walls are straight.

In variations thereof, the further embodiments include embodiments in which the first link is connected to a linear actuator.

In variations thereof, the further embodiments include embodiments in which the free lever element is forced by a return spring.

It is, thus, apparent that there is provided, in accordance with the present disclosure, flow restriction devices methods and systems. Many alternatives, modifications, and variations are enabled by the present disclosure. Features of the disclosed embodiments can be combined, rearranged, omitted, etc., within the scope of the invention to produce additional embodiments. Furthermore, certain features may sometimes be used to advantage without a corresponding use of other features. Accordingly, Applicants intend to embrace all such alternatives, modifications, equivalents, and variations that are within the spirit and scope of the present invention.

What is claimed is:

1. A flow restrictor, comprising:
a flexible tube held in a housing;
a linear actuator connected through an intermediate link to a distal link via a first revolute joint proximate the linear actuator and a second revolute joint connecting the intermediate link and the distal link;

the distal link having a distal end adjacent the flexible tube; and
the intermediate link and the distal link being constrained to move such that when the linear actuator moves the first revolute joint toward the linear actuator, the distal end of the distal link is driven into a side of the flexible tube thereby progressively occluding the flexible tube, wherein
the first revolute joint and the second revolute joint each have a roller guided by walls of a chamber thereby constraining movement of the intermediate link and the distal link.

2. The flow restrictor of claim 1, wherein the distal link has a roller at an end thereof.

3. The flow restrictor of claim 1, wherein the linear actuator includes an effecter and the effecter is a rod that is forced by the linear actuator in opposing directions under command of a controller.

4. The flow restrictor of claim 1, wherein
the walls of the chamber include a first wall, a second wall, and a third wall,
the first wall is substantially parallel to the second wall,
the third wall is substantially perpendicular to the second wall,
the roller of the first revolute joint is positioned to come into contact with the first wall, and
the roller of the second revolute joint is positioned to come into contact with the third wall.

5. The flow restrictor of claim 4, further comprising:
a biasing spring attached to the second wall and positioned to exert a force on the second revolute joint, the force having a direction parallel to the third wall.

6. The flow restrictor of claim 3, wherein
the walls of the chamber include a first wall, a second wall, and a third wall,
the first wall is substantially parallel to the second wall,
the third wall is substantially perpendicular to the second wall,
the roller of the first revolute joint is positioned to come into contact with the first wall,
the roller of the second revolute joint is positioned to come into contact with the third wall, and
the effecter enters the chamber through a gap between the first wall and the third wall.

* * * * *